United States Patent
Fleissman et al.

(10) Patent No.: US 8,128,919 B2
(45) Date of Patent: Mar. 6, 2012

(54) LONG-WEARING COSMETIC COMPOSITION

(75) Inventors: Leona G. Fleissman, Ridgewood, NJ (US); Maha Raouf, Franklin Lakes, NJ (US)

(73) Assignee: Avon Products, Inc, New York, NY (US)

( * ) Notice: Subject to any disclaimer, the term of this patent is extended or adjusted under 35 U.S.C. 154(b) by 1172 days.

(21) Appl. No.: 11/814,260

(22) PCT Filed: Apr. 20, 2006

(86) PCT No.: PCT/US2006/014919
§ 371 (c)(1),
(2), (4) Date: Jul. 18, 2007

(87) PCT Pub. No.: WO2006/113882
PCT Pub. Date: Oct. 26, 2006

(65) Prior Publication Data
US 2008/0107695 A1    May 8, 2008

Related U.S. Application Data

(60) Provisional application No. 60/673,113, filed on Apr. 20, 2005.

(51) Int. Cl.
*A61Q 1/00* (2006.01)
*A61Q 1/04* (2006.01)
*A61Q 1/06* (2006.01)

(52) U.S. Cl. .......... 424/78.03; 424/64; 424/401

(58) Field of Classification Search .......... None
See application file for complete search history.

(56) References Cited

U.S. PATENT DOCUMENTS

| | | | |
|---|---|---|---|
| 4,122,023 A | 10/1978 | Yasui et al. | |
| 5,505,937 A | 4/1996 | Castrogiovanni et al. | |
| 5,948,393 A | 9/1999 | Tomomasa et al. | |
| 6,258,348 B1 * | 7/2001 | Tsivkin | 424/70.12 |
| 6,277,386 B1 | 8/2001 | Kim et al. | |
| 6,309,629 B1 | 10/2001 | Travkina et al. | |
| 6,312,672 B1 | 11/2001 | Coolbaugh et al. | |
| 6,471,983 B1 | 10/2002 | Veeger et al. | |
| 7,749,524 B2 * | 7/2010 | Lu et al. | 424/401 |
| 2004/0191197 A1 | 9/2004 | Main et al. | |
| 2005/0238611 A1 * | 10/2005 | Rando et al. | 424/70.122 |
| 2007/0154440 A1 * | 7/2007 | Fleissman et al. | 424/70.122 |

FOREIGN PATENT DOCUMENTS

| | | |
|---|---|---|
| JP | A-61-65809 | 4/1986 |
| WO | A-602905 | 6/1994 |

* cited by examiner

*Primary Examiner* — Jyothsna Venkat
(74) *Attorney, Agent, or Firm* — Joan M. McGillycuddy; Charles J. Zeller

(57) ABSTRACT

The present invention relates to a cosmetic composition particularly useful for the application of color such as in a foundation, lip gloss, lip stick, mascara, eye shadow, blush, and nail polish, for example. A cosmetic composition according to the present invention includes a film-forming silicone-containing polyurethane having a viscosity from about 130,000 to about 2,500,000 cps, preferable from about 400,000 to about 2,500,000 cps and most preferably from about 750,000 to about 2,500,000.

1 Claim, No Drawings

LONG-WEARING COSMETIC COMPOSITION

This application claims priority to International Application Ser. No. PCT/US06/14919 filed Apr. 20, 2006, which claims priority to U.S. Provisional Application No. 60/673,133 field Apr. 20, 2005.

The present invention relates to a cosmetic composition particularly useful for the application of color such as in a foundation, lip gloss, lip stick, mascara, eye shadow, blush, and nail polish, for example. A cosmetic composition according to the present invention includes a film-forming silicon-containing polyurethane having a viscosity from about 130,000 to about 2,500,000 cps, preferable from about 400,000 to about 2,500,000 cps and most preferably, from about 750,000 to about 2,500,000. The cosmetic composition according to the present invention also contains cosmetic excipients as are known in the art, colorants, and other cosmetic additives. It was surprisingly found that by including the film-forming silicone containing-polyurethane in a cosmetic composition, a more comfortable, less tacky and longer wearing film was formed on the surface to which the composition was applied.

FIELD OF THE INVENTION

The present invention relates to cosmetic compositions. More particularly, it relates to cosmetic compositions including a film-forming silicone-containing polyurethane having a viscosity from about 130,000 to about 2,500,000 cps, more preferably, from about 400,000 to about 2,500,000 cps, and most preferably, from about 750,000 to about 2,500,000. Preferably, the film-forming silicone-containing polyurethane has an isocyanate content of about 10 ppm or less, as measured by the presence of NCO groups.

BACKGROUND OF THE INVENTION

It has long been considered desirable to provide cosmetic lip products, such as lipstick and lip gloss, which impart a transfer resistance to the lips. Conventionally, cosmetic lip products comprise pigments dispersed in a base of fats or oils with various waxes added to provide the desired consistency of the product.

Cosmetic products for make-up of face, lips, eyelashes etc often suffer from the drawback that, when they come into contact with e.g. the fingers or clothing, they tend to smudge or soil these surfaces. Consequently, in order to avoid these problems cosmetic products which have high adhesive properties and which provide for the deposition of a continuous, long-lasting film onto e.g. the facial skin, the lips, the eyelashes etc are of particular interest.

Lipstick and make-up foundation compositions normally contain fatty substances such as oils, viscous compounds and waxes, as well as particulate phase usually composed of fillers and pigments. When applied to the skin or lips, these compounds have the disadvantage of being transferred, that is, of forming a deposit, at least in part, while leaving a trace on objects with which they come into contact, in particular, a glass, a cup, a piece of clothing or the skin. Consequently, there remains on the skin or lips a reduced film which requires the periodic re-application of the make-up foundation or lipstick composition.

Furthermore, the appearance of unacceptable traces on clothing and, most especially, on the necks of blouses, may dissuade some women from using this type of make-up.

Another disadvantage of these compositions lies in the problem of migration. Indeed, it has been observed that some foundation compositions tended to spread inside wrinkles in the skin, that some lipstick compositions traveled in the small wrinkles surrounding the lips, while eye-shadows tended to spread in the folds of the eyelids. In the case of eye-shadows, the appearance of lines in the make-up, caused by movements of the eyelids, were also noted. All of these phenomena produced an unaesthetic effect which the consumer quite obviously wished to avoid.

In the prior art these problems have been recognized and proposals have been made to reduce these problems. Thus, in U.S. Pat. No. 5,948,393 (Tomomasa, et al.) a long-lasting cosmetic composition is described which contains inter alia an oil-soluble film-forming resin. This resin can be one of many types, among which is also mentioned polyisoprene. No specification of the molecular weight of the polyisoprene is given. In U.S. Pat. No. 6,471,983 (Veeger, et al.) a cosmetic composition for skin is described which contains a polyisoprene latex, but no specification of the molecular weight of the polyisoprene latex is given. In U.S. Pat. No. 4,122,023 (Yasui, et al.) a synthetic saturated oil for lubricants and cosmetics is described which is prepared from a hydrogenated polyisoprene with a low molecular weight of between 290 and 3,000. In U.S. Pat. No. 6,312,672 (Coolbaugh, et al.) a sunscreen composition is described which contains a polymer or copolymer of isoprene, butadiene and styrene. Selectively hydrogenated isoprene/butadiene copolymers are preferred. Polymers of conjugated dienes may also be used, and they may be partially, selectively or completely hydrogenated. Their molecular weight may range from 5,000 to 35,000, with a maximum 50,000.

Published U.S. Patent Application No. 20040191197 (assigned to Intercos S.p.A) describes the use of an unhydrogenated polyisoprene with a molecular weight of between 100,000 and 4,000,000 in cosmetic products and the use of an oleophilic modified clay in such products.

Efforts to improve the durability and transfer resistance of cosmetic lip color products have focused on the use of polymeric film formers. For example, U.S. Pat. No. 5,505,937 discloses lipstick compositions comprising volatile solvents, silicone resins, wax, powder and oil which are said to be transfer resistant by the "Kiss test."

U.S. Pat. No. 6,309,629 discloses cosmetic compositions, such as lip gloss, which are smooth, glossy and wear resistant.

For several years, many cosmeticians have been interested in lipsticks, and, more recently, make-up foundation compositions, that "did not transfer." Thus, Patent Application No. JP-A-61-65809 disclosed "transferless" lipstick compositions containing 1 to 70% by weight of a liquid silicone resin incorporating repeating silicate patterns (or having a three-dimensional lattice) comprising alkylated suspended chains of 1 to 6 atoms of carbon or phenylated chains, 10 to 98% by weight of a volatile silicone oil having a cyclic Si—O chain and containing methyl radicals, and pulverulent fillers.

Patent Application No. EP-A-602905 disclosed "transferless" lipsticks containing a volatile cyclic or linear silicone containing suspended methylated chains and a silicone resin incorporating a suspended esterified chain having at least 12 atoms of carbon. The lipstick film still possesses the problem of being uncomfortable when applied and, most notably, of being too dry.

To date, efforts to provide transfer resistant lip product have met with only moderate success, however. Commercial transfer resistant lip products have been reported to be uncomfortable to wear and may have a drying effect on the lips. Further, the finish which is sought in lip products has not satisfactorily been replicated in transfer resistant products.

These compositions, although highly satisfactory as regards the lack of transference, had the disadvantage of being in liquid form and thus inconvenient to use, or, at the very least, of being far removed from the conventional idea of a lipstick, thereby limiting the number of women prepared to use this type of lipstick. In addition, the film produced on the lips after evaporation of the silicone oil had the disadvantage of becoming uncomfortable over time (sensation of drying and tugging, thus dissuading still other women from using this type of lipstick). To enhance the comfort given by this type of composition, non-volatile oils, whether or not they contained silicone, could be added; however, in this case the "transferless" property is lost. Moreover, these compositions take a long time to dry; that is, the lack of transfer appears only after several minutes.

What is yet needed to a cosmetic composition that imparts a long-wearing color to the end user, such as in a lip gloss, mascara, eye shadow, foundation, nail enamel and the like. The invention is intended to form a film that does not transfer or migrate and that does not stain an object with which it comes into in contact, while exhibiting improved cosmetic "transferless" properties in combination with a smooth sliding, the absence of tugging, and the lack of drying of the skin to which the composition is applied, such as to the lips.

SUMMARY OF THE INVENTION

In accordance with the foregoing objectives and others, the present invention overcomes the deficiencies in the prior art by providing compositions and methods for forming long-wearing films on the body, including lips, skin, nail, and the like.

It was surprisingly found that the inclusion of a film-forming silicone-containing polyurethane having a viscosity from about 130,000 to about 2,500,000 cps, preferably from about 400,000 to about 2,500,000 cps, provides long-lasting film-forming and non-transfer properties when applied as a cosmetic composition, such as in the form of a lip color, foundation, mascara, nail enamel and the like.

In one aspect of the invention, a cosmetic composition, such as, for example, a lip product, is provided comprising a film-forming polyurethane polymer having a weight average molecular weight of at least about 50,000, the polyurethane polymer being present in an effective amount to impart long lasting, comfortable film when applied to a surface of the human body, such as the lips. In various implementations, the polyurethane polymer will have a weight average molecular weight of at least about 75,000, or at least about 100,000. The viscosity of the polyurethane polymer will typically range from about 130,000 to about 2,500,000 cps, preferably from about 400,000 to about 2,500,000 cps, and most preferably from about 750,000 to about 2,500,000.

A suitable film-forming silicone-containing polyurethane includes diisocyanate moieties in an amount of about 10 ppm or less, as measured by the presence of NCO groups. Suitable film-forming silicone-containing polyurethanes can be formed from bis-PEG-1 dimethicone-bis hydroxyl polydimethyl siloxane/IPDI copolymer, bis-PEG-1 dimethicone, bis-hydroxy polydimethyl siloxane and isophorone diisocyanate; and from bis-PEG-1 dimethicone-polypropylene glycol-26/IPDI copolymer, bis-PEG-1 dimethicone, and isophorone diisocynate and combinations thereof. Suitable film forming silicone-containing polyurethanes can be obtained from Alzo International, Inc., under the trade designations of Polyderm PPI-SI-LL and Polyderm PPI-SI-G.

In another aspect of the invention, a method is provided for forming a cosmetic film on a surface of the body, such as the lips, comprising applying thereto a composition comprising the polyurethane polymers described above in an effective amount to impart a long-wearing, comfortable film on the surface.

The amount of these film-forming polymers to be incorporated into the cosmetic composition according to the present invention is preferably 0.1 to 60% by weight, particularly 0.2 to 40% and preferably from about 5% to 20% by weight of the cosmetic product, depending upon the desired end use of the cosmetic composition. For example, if the desired end use of the cosmetic composition is a lip color composition, such desired properties include ease of application, length of drying time, aesthetic feel to the user's lips, and the like. Thus, preferably, in a lip color composition, the amount of the film-forming silicone-containing polyurethane is from about 10 to about 30% by weight.

It is believed that cosmetic compositions of the present invention that include a film-forming silicone-containing polyurethane, when applied to the skin, eyelashes or lips, advantageously exhibit a sustaining film capable of withstanding deposition of its traces on certain substrates with which they may be brought into contact, in particular a glass, a cup, a cigarette, an item of clothing or the skin. Thus, persistence of the applied film is achieved which does not require the regular renewal of the application of the composition, in particular a foundation or lipstick composition. In point of fact, it is the wish of users today to beautify their faces, including the lips, and their bodies while spending the least possible time doing so. Furthermore, the appearance of these unacceptable traces, in particular on blouse collars, can dissuade some women from using this type of make up.

These and other aspects of the present invention will become apparent to those skilled in the art after a reading of the following detailed description of the invention, including the illustrative embodiments and examples.

DETAILED DESCRIPTION OF THE INVENTION

All terms have their ordinary meaning in the art unless otherwise defined herein. As used herein, the term "diol" is intended to include any molecule have at least two hydroxyl groups available to react with diisocyante. The term "diol" does not exclude the possibility of additional hydroxyl groups also being present, and therefore specifically includes polyols and the like. The term "effective amount" refers to that amount of polyurethane polymer necessary to provide a transfer resistant continuous film on the surface of the lips and preferably last for at least about two hours, more preferably at least about four hours, most preferably at least about six hours, and more preferred still at least about eight hours, comfortably under normal activity without the need for re-application. The "effective amount" will typically be about 0.1 to about 60% by weight, particularly from about 2 to about 40% by weight, and preferably from about 5 to about 20% by weight of the cosmetic product.

An essential component of the inventive cosmetic formulations is a high molecular weight, high viscosity polyurethane polymer which acts as a film former. In the broadest aspect of the invention, it is contemplated that any polyurethane polymer will be suitable. The polyurethane polymer will typically have a weight average molecular weight greater than about 50,000, preferably greater than about 75,000, and more preferably greater than about 100,000. The viscosity of the polyurethane polymer will typically range from about 130,000 to about 2,500,000 cps, preferably from about 400,000 to about 2,500,000 cps, and more preferably from about 750,000 to about 2,500,000 cps.

It has surprisingly been found that inclusion of these film-forming high molecular weight, high viscosity polyurethane polymers in cosmetic compositions provides films that are more comfortable, less tacky, longer-wearing, and have enhanced transfer resistant properties as compared to conventional film forming polymers.

The polyurethane polymers of the invention are typically obtained by the reaction of a diisocyanate component with a diol component according to methods well-known in the art. Suitable diisocyante and diol components are discussed below.

a. Diisocyanate Component

The diisocyante will have the general form O—C—N—R—N—C—O where R represents an optionally substituted, branched or straight chain substituent comprising alkyl groups, aryl groups, or combinations of alkyl and aryl groups. R may therefore include alkyl, cycloalkyl, alkyl-cycloalkyl, aryl, alkyl-aryl, aryl-aryl, aryl-alkyl-aryl, and the like. Specific diisocyantes contemplated to be useful include, without limitation, toluene diisocyante (TDI), methylene diphenyl diisocyanate (MDI), hexamethylene diisocyanate (HDI), 1,5-napthalene diisocyante (NDI), p-phenylene diiosocyanate (PPI), isophorone diisocyanate (IPDI), and the like. Isophorone diisocyante (IPDI), shown below, is the currently preferred diisocyanate for preparing the polyurethane polymers according to the invention.

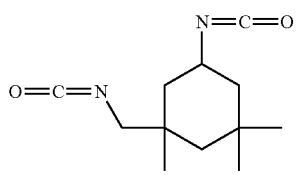

b. Diol Component

There is essentially no constraint on the selection of the diol component. The diol component will typically comprise a straight chain or branched spacer having hydroxyl functional groups at both terminal ends, optionally containing one or more unsaturated bonds and optionally containing one or more heteroatoms. The diol can be, for example, an alkyl diol, polyether polyol, polyester polyol, polyesteramide polyol, polythioether polyol, polycarbonate polyol, polyacetal polyol, polyolefin polyol, and the like.

Suitable alkyl diol, include without limitation, $C_3$ to $C_{30}$ alkyl diols such as, for example, 1,6-dihydroxyhexane, 1,7-dihryoxyheptane, 1,8-dihyroxyoctane, 1,9-dihydroxynonane, 1,10-dihydroxydecane, myristyl alcohol dimer, isocetyl alcohol dimer, isostearyl alcohol dimer, laureth-3 alcohol dimer, octyldodecyl alcohol dimer, and the like.

Suitable polyether diols include polyalkylene oxide diols of the form HO—$(R_1$—O$)_n$—H where $R_1$ represents a branched or straight chain alkyl group having from two to ten carbon atoms, preferable from two to three carbon atoms, and where n is an integer from 2 to about 200, preferably from 2 to about 100, and more preferably from about 2 to about 50. More preferably, the diol is of the form HO—(CH$_2$CHR$_2$—O)$_n$—H where $R_2$ represents H (polyethylene glycol, PEG) or CH$_3$ (polypropylene glycol, PPG). It is contemplated that random, alternating, and block copolymers of ethylene glycol and propylene glycol will also be useful.

The diol component may comprise a polyester glycol, including, for example, products obtained by polycondensing aliphatic dicarboxylic acids with a glycol. Exemplary aliphatic dicarboxylic acids include succinic acid, malonic acid, glutaric acid, adipic acid, pimelic acid, suberic acid, azelaic acid, sebacic acid, dodecanedicarboxylic acid, and cyclohexanedicarboxylic acid. Glycols include, without limitation ethylene glycol, propylene glycol, 1,4-butanediol, 1,6-hexanediol, cyclohexane dimethanol, neopentylene glycol, pentaerythritol, polyether glycols, and the like.

The diol may also be an organosiloxane diol of the form:

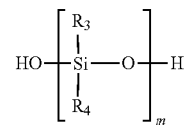

where m is an integer from 2 to about 5,000, preferably from 2 to about 2,500, and more preferably from about 2 to about 1,000; and where $R_3$ and $R_4$ are independently selected, at each occurrence, from the group consisting of substituted or unsubstituted branched or straight chain $C_1$-$C_{10}$ alkyl, alkenyl, or alkynyl group, including without limitation methyl, ethyl, propyl, isopropyl, butyl, isobutyl, t-butyl, pentyl, hexyl, vinyl, allyl, butenyl, pentenyl, hexenyl, propynyl, butynyl, n-pentyl, iso-pentyl, neo-pentyl, tert-pentyl, cycloalkyl, heterocycloalkyl, haloalkyl, benzyl, alkyl-aryl, substituted or unsubstituted aryl or heteroaryl groups, $C_1$-$C_6$ alkoxy, amino, hydroxyl, hydrido, carboxy, cyano, or halogen. Preferably, $R_3$ and $R_4$ are independently selected from the group consisting of $C_1$-$C_6$ alkyl groups, and more preferably, $C_1$-$C_3$ alkyl groups. In a currently preferred embodiment, at least one of $R_3$ and $R_4$ is methyl, and even more preferably, both $R_3$ and $R_4$ are methyl. In the case where both $R_3$ and $R_4$ are methyl, the organosiloxane polymer will be a polydimethylsiloxane, commonly known as a dimethicone.

The organosiloxane polymer may further comprise monomers having branching points of the T or Q type. When present, the T and Q structures will typically represent less than about 50%, preferably less than about 20%, and more preferably less than about 10% of the total repeat units in the organopolysiloxane polymer.

Other interesting diols may be prepared by the addition of polyalkylene oxide diols, such as PEG or PPG, to any of the foregoing diols. For example, hydroxy carboxylic acids, such as hydroxyl caproic acid, may be esterified with polyalkylene glycols to provide diols. Similarly, useful diols are obtained by transesterification of lactones such as butyrolactone and caprolactone with polyalkylene glycols.

Particular mention may be made of block copolymers of polyalkylene glycols, such as PEG, with the organosiloxane diols described above. In one such embodiment, the diol component is a copolymer of a first component having the form —$(R_1$—O$)_n$—H and a second component comprising a diol derived from an organosiloxane polymer. One exemplary copolymer has the form:

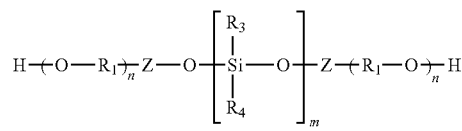

where n, m, $R_1$, $R_4$ are defined as above, and wherein Z represents a bond or a spacer group comprising from one to ten carbon atoms and optionally including one or more heteroatoms. Preferably, Z is a group of the form:

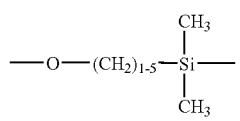

The copolymer is preferably of the form ABA where A represents the polyalkylene glycol component and B represents the polyorganosiloxane component, but may also be, for example, a copolymer of the form AB, BAB, ABAB, and the like. Such polymers will include those known in the art as bis-PEG-dimethicone diols.

In a particularly interesting variant, the bis-PEG-dimethicone diol will have the structure: where m and n are as defined above. This compound has been assigned the Chemical Abstracts registry number CAS#102783-01-7.

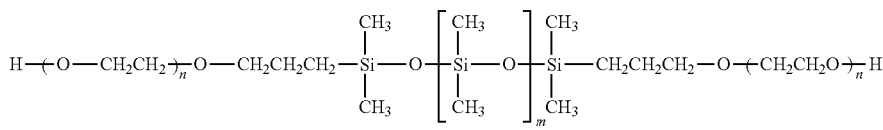

The urethane polymers according to the invention may also be derived from mixtures of diols and mixtures of diisocyanates and may be block, alternating, or statistical copolymers.

c. Preferred Polyurethanes

The following structure is illustrative of the currently preferred polyurethane polymers according to the invention:

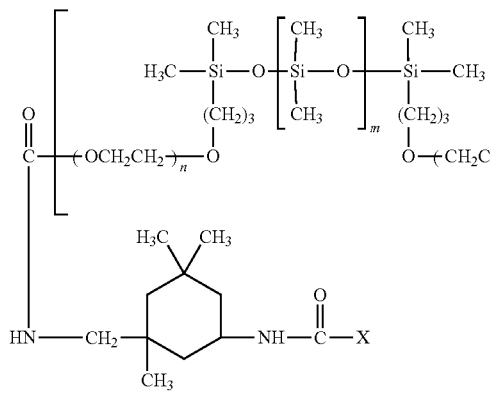 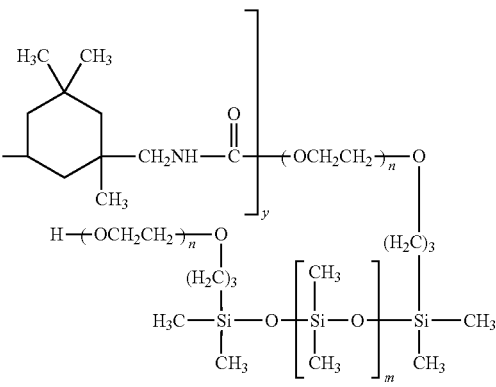

where n and m are as defined above, y represents the degree of polymerization, and X is a terminating group.

Y is selected to provide a polymer having a weight average molecular weight greater than about 50,000, preferably greater than about 75,000, and more preferably greater than about 100,000 and a viscosity ranging from about 130,000 to about 2,500,000 cps, preferably from about 400,000 to about 2,500,000 cps and most preferably, from about 750,000 to about 2,500,000 cps.

There is essentially no restriction on the selection of the terminal group X. X may be selected to modify one or more properties of the polymer, including lipophilicity, water solubility, tack, viscosity, and the like. Preferably, X will comprise a hydroxyl group or other functional group that is reactive with the isocyanate functionally. Therefore, X may represent, without limitation, an alcohol, a diol, or a polyol, including for example, any of diols described herein.

In one exemplary embodiment, X represents the polypropylene glycol, PPG-26. In the case where X is PPG-26, the polyurethane polymer has been given the proposed INCI name bis-PEG-1 dimethicone-polypropylene glycol-26/IPDI copolymer and is commercially available from Alzo International under the name Polyderm™ PPI-SI-G.

The polyurethane polymers may be incorporated into any cosmetic formulation. While the high viscosity polyurethanes of the invention are ideally suited for lip products, nail enamels, and mascara because they impart the long-wearing transfer resistant benefits, it is contemplated that they will be useful in formulating other cosmetic compositions as well, including without limitation, foundation, eye shadow, blush and the like, where long-wearing properties are desired. It is within the skill in the art to formulate any such cosmetic product with the polyurethane polymers described herein.

The amount of these film-forming polyurethane polymers to be incorporated into the cosmetic formulations of the present invention is typically from about 0.1 to 60% by weight, particularly from about 2 to 40% by weight, and preferably from about 5 to about 20% by weight.

Other Components:

The compositions will typically comprise one or more coloring agents. The composition of the present invention provides a long-wearing comfortable film for application of color to various tissue types. Thus, a composition according to the present invention preferably includes a colorant that can be selected from lipophilic dyes, hydrophilic dyes, pigments and pearlescent agents commonly used in cosmetic or dermatological compositions, and their mixtures. This colorant is generally present in a proportion of 0.01 to 50% of the total weight of the composition, preferably of 2 to 30%, if it is present, and better still of 5 to 20%.

The fat-soluble dyes are, for example, Sudan red, DC Red 17, DC Green 6, beta-carotene, soybean oil, Sudan brown, DC Yellow 11, DC Violet 2, DC Orange 5, quinoline yellow or annalto. They can represent from 0.1 to 20% of the weight of the composition and better still from 0.1 to 6%.

The pigments can be white or colored, inorganic and/or organic and coated or uncoated. Mention may be made, among inorganic pigments, of titanium or zinc dioxide, optionally treated at the surface, zirconium or cerium oxides, iron or chromium oxides, manganese violet, ultramarine blue, chromium hydrate and ferric blue. Mention may be made, among organic pigments, of carbon black, pigments of D & C type and lakes based on cochineal carmine or on barium, strontium, calcium or aluminum. The pigments can represent from 0.1 to 50% and better still from 2 to 30% of the total weight of the composition, if they are present.

It is within the skill in the art to choose coloring agents and combinations of coloring agents to produce a desired color. Suitable coloring agents, including pigments, lakes, and dyes, are well known in the art and are disclosed in the C.T.F.A., International Cosmetic Ingredient Dictionary and Handbook, 10$^{th}$ Edition, 2004, the contents or which are hereby incorporated by reference. Organic pigments include, for example, FD&C dyes, D&C dyes, including D&C Red, Nos. 2, 5, 6, 7, 10, 11, 12, 13, 30 and 34, D&C Yellow No. 5, Blue No. 1, Violet No. 2. Exemplary inorganic pigments include, but are not limited to, metal oxides and metal hydroxides such as magnesium oxide, magnesium hydroxide, calcium oxide, calcium hydroxides, aluminum oxide, aluminum hydroxide, iron oxides ($\alpha$—$Fe_2O_3$, y—$Fe_2O_3$, $Fe_3O_4$, FeO), red iron oxide, yellow iron oxide, black iron oxide, iron hydroxides, titanium dioxide, titanium lower oxides, zirconium oxides, chromium oxides, chromium hydroxides, manganese oxides, cobalt oxides, cerium oxides, nickel oxides and zinc oxides and composite oxides and composite hydroxides such as iron titanate, cobalt titanate and cobalt aluminate. Other suitable colorants include ultramarine blue (i.e., sodium aluminum silicate containing sulfur). Prussian blue, manganese violet, bismuth oxychloride, talc, mica, sercite, magnesium carbonate, calcium carbonate, magnesium silicate, aluminum magnesium silicate, silica, titanated mica, iron oxide titanated mica, and the like. The colorants may be surface modified with, for example, fluoropolymers, to adjust one or more characteristics of the colorant as described in, for example, U.S. Pat. Nos. 6,471,950, 5,482,547 and 4,832,944, the contents of which are hereby incorporated by reference. Suitable pearling pigments include without limitation bismuth oxychloride, guanine and titanium composite materials containing, as a titanium component, titanium dioxide, titanium lower oxides or titanium oxynitride, as disclosed in U.S. Pat. No. 5,340,569, the contents of which are hereby incorporated by reference. Other suitable pearlescent materials typically are pigments or layers of titanium dioxide on a substrate such as mica, polyethylene terephthalate, bismuth oxychloride, aluminum oxide, calcium borosilicate, synthetic flourophlogopite (synthetic mica), silica, acrylates copolymer, methyl methacrylate, and the like.

The pearlescent pigments can be chosen from white pearlescent pigments, such as mica covered with titanium or with bismuth oxychloride, colored pearlescent pigments, such as titanium oxide-coated mica with iron oxides, titanium oxide-coated mica with in particular ferric blue or chromium oxide, or titanium oxide-coated mica with an organic pigment of the abovementioned type, and pearlescent pigments based on bismuth oxychloride. They can represent from 0.1 to 20% of the total weight of the composition and better still from 0.1 to 15%, if they are present.

The coloring/pearling agents can represent from 0.1 to 50% and better still from 2 to 30% of the total weight of the composition.

The cosmetic compositions may further comprise one or more waxes, fats, and emollients to provide the desired body to the product. The fats may be natural animal and vegetable fats and oils, and semi-synthetic fats and oils, examples of which include avocado oil, linseed oil, almond oil, Chinese wax, perilla oil, olive oil, cacao butter, kapok wax, kaya oil, carnauba wax, liver oil, candellila wax, beef tallow, beef foot oil, beef bone fat, hydrogenated beef tallow, apricot kernel oil, spermaceti, hydrogenated oil, wheat germ oil, sesame oil, rice germ oil, rice bran oil, sugar can wax, sasanqua oil, safflower oil, shea butter, Chinese tung oil, cinnamon oil, jojoba wax, shellac wax, turtle oil, soybean oil, tea seed oil, tsubaki oil, evening primrose oil, corn oil, lard, rape seed oil, Japanese tung oil, rice-bran wax, germ oil, horse fat, persic oil, palm oil, palm kernel oil, castor oil, hydrogenated castor oil, caster oil fatty acid methyl ester, sunflower oil, grape seed oil, bayberry wax, jojoba oil, macadamia nut oil, bees wax, mink oil, cottonseed oil, cotton wax, Japan wax, haze kernel oil, montan wax, coconut oil, hydrogenated coconut oil, tri-coconut oil fatty acid glyceride, mutton-tallow, peanut oil, lanolin, liquid lanolin, reduced lanolin, lanolin alcohol, hard lanolin, lanolin acetate, lanolin fatty acid isopropyl, hexyl laurate, POE lanolin alcohol ether, POE lanolin alcohol acetate, lanolin fatty acid polyethylene glycol, POE hydrogenated lanolin alcohol ether, and egg yolk oil. Additionally, the term "POE" as used herein stands for polyoxyethylene.

The cosmetic compositions of the invention may optionally comprise other active and inactive ingredients, including, but not limited to, cosmetically acceptable carriers, oils, sterols, amino acids, moisturizers, powders, ultraviolet absorbents, colorants (including pigments and/or dyes) pH adjusters, perfumes, essential oils, cosmetic active ingredients, vitamins, essential fatty acids, sphingolipids, self-tanning compounds such as DHA, sunscreens, excipients, fillers, emulsifying agents, antioxidants, surfactants, film formers, chelating agents, gelling agents, thickeners, emollients, humectants, moisturizers, vitamins, minerals, viscosity and/or rheology modifiers, sunscreens, keratolytics, depigmenting agents, retinoids, hormonal compounds, alpha-hydroxy acids, alpha-keto acids, anti-mycobacterial agents, antifungal agents, antimicrobials, antivirals, analgesics, lipidic compounds, anti-allergenic agents, H1 or H2 antihistamines, anti-inflammatory agents, anti-irritants, antineoplastics, immune system boosting agents, immune system suppressing agents, anti-acne agents, anesthetics, antiseptics, insect repellents, skin cooling compounds, skin protectants, skin penetration enhancers, exfolients, lubricants, fragrances, colorants, staining agents, depigmenting agents, hypopigmenting agents, preservatives, stabilizers, pharmaceutical agents, photostabilizing agents, spherical powders and mixtures thereof. In addition to the foregoing, any other compound for the treatment of skin disorders may be included.

The cosmetic composition according to the present invention may be prepared in any form, such as a solubilization system, emulsification system, powder-dispersed solubilization system, powder-dispersed emulsification system or powder-dispersed oil system, in accordance with a method known per se in the art, and can be used for a make-up cosmetic such as a foundation, powder, lip color, cheek rouge, eye shadow or nail enamel.

The pH of the external skin care composition according to the present invention is preferably adjusted to 2 to 11, particularly 3 to 9.

Compositions of the present invention that contain hydrophobic components and are frequently fashioned in the form of emulsions. Emulsions comprise a hydrophilic phase comprising the thickened particulate-containing hydrophilic liquid carrier or other hydrophilic diluent, and a hydrophobic phase comprising a hydrophobic component, e.g., a lipid, oil or oily material. As well known to one skilled in the art, the hydrophilic phase will be dispersed in the hydrophobic phase, or vice versa, to form respectively hydrophilic or hydrophobic dispersed and continuous phases, depending on the composition ingredients. In emulsion technology, the term "dispersed phase" is a term well-known to one skilled in the art which means that the phase exists as small particles or droplets that are suspended in and surrounded by a continuous phase. The dispersed phase is also known as the internal or discontinues phase. The emulsion may be or comprise (e.g., in a triple or other multi-phase emulsion) an oil-in-water emulsions typically comprise from about 1% to about 50% (preferably about 1% to about 30%) of the dispersed hydrophobic phase and from about 1% to about 98% (preferably from about 40% to about 90%) of the continuous hydrophilic phase; water-in-oil emulsions typically comprise from about 1% to about 98% (preferably from about 40% to about 90%) of the dispersed hydrophilic phase and from about 1% to about 50% (preferably about 1% to about 30%) of the continuous hydrophobic phase. The emulsion may also comprise a gel network, such as described in G. M. Eccleston, Application of Emulsion Stability Theories to Mobile and Semisolid O/W Emulsions, Cosmetics & Toiletries, Vol. 101, November 1996, pp. 73-92. Preferred emulsions have an apparent viscosity of from about 5,000 to about 200,000 centipoise (cps).

The emulsion may contain an emulsifier and/or surfactant, generally to help disperse and suspend the discontinuous phase within the continuous phase. A wide variety of such agents can be employed. Known or conventional emulsifiers/surfactants can be used in the composition, provided that the selected agent is chemically and physically compatible with essential components of the composition, and provides the desired dispersion characteristics.

As mentioned above, the compositions herein may contain a wide variety of optional ingredients that perform one or more functions useful in products of this type. Such optional components may be found in either the thickened hydrophilic phase or the optional hydrophobic phase(s) or in one or more additional phases of the composition herein. Nonexclusive examples of such materials are described in Harry's Cosmeticoloy, 7th Ed., Harry & Wilkinson (Hill Publishers, London 1982); in Pharmaceutical Dosage Forms-Disperse Systems; Lieberman, Rieger & Banker, Vols. 1 (1988) & 2 (1989); Marcel Decker, Inc., in The Chemistry and Manufacture of Cosmetics, 2nd Ed., deNavarre (Van Nostrand 1962-1965); and in The Handbook of Cosmetic Science and Technology, 1st Ed. Knowlton & Pearce (Elsevier 1993). Such ingredients include, but are not limited to, transparent particulates; skin conditioning agents such as emollients, humectants, and moisturizers; skin cleansers; skin care actives such as vitamin B3 compounds, retinoids, anti-oxidants/radical scavengers, and organic hydroxy acids; structuring agents; and other actives including anti-inflammatory agents, sunscreens/sunblocks, chelators, desquamation agents/exfoliants, and skin lightening agents.

In an embodiment, the compositions of the present invention may contain a retinoid. The retinoid enhances the skin appearance benefits of the present invention, especially in regulating skin condition, including regulating signs of skin aging, more especially wrinkles, lines, and pores. As used herein, "retinoid" includes all natural and/or synthetic analogs of Vitamin A or retinol-like compounds which possess the biological activity of Vitamin A in the skin as well as the geometric isomers and stereoisomers of these compounds. The retinoid is preferably retinol, retinol esters (including retinyl palmitate, retinyl acetate, retinyl propionate), retinal, and/or retinoic acid (including all-trans retinoic acid and/or 13-cis-retinoic acid), more preferably retinoids other than retinoic acid. These compounds are well known in the art and are commercially available from a number of sources, e.g., Sigma Chemical Company (St. Louis, Mo.), and Boerhinger Mannheim (Indianapolis, Ind.). One or more retinoids may be used herein including retinol, retinyl palmitate, retinyl acetate, retinyl proprionate, retinal and combinations thereof.

The retinoid may be included as the substantially pure material, or as an extract obtained by suitable physical and/or chemical isolation from natural (e.g., plant) sources. The retinoid is preferably substantially pure, more preferably essentially pure. The compositions of this invention may contain a safe and effective amount of the retinoid, such that the resultant composition is safe and effective for regulating skin condition, preferably for regulating visible and/or tactile discontinuities in skin, more preferably for regulating signs of skin aging, even more preferably for regulating visible and/or tactile discontinuities in skin texture associated with skin aging. The compositions may contain from about 0.005% to or about 2%, more preferably 0.01% to or about 2%, retinoid.

A composition of the present invention may include an anti-oxidant/radical scavenger. The anti-oxidant/radical scavenger is especially useful for providing protection against UV radiation which can cause increased scaling or texture changes in the stratum corneum and against other environmental agents which can cause skin damage. A safe and effective amount of an anti-oxidant/radical scavenger may be added to the compositions of the subject invention, preferably from about 0.1% to about 10%, more preferably from about 1% to about 5%, of the composition.

Anti-oxidants/radical scavengers such as ascorbic acid (vitamin C) and its salts, ascorbyl esters of fatty acids, ascorbic acid derivatives (e.g., magnesium ascorbyl phosphate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolox®, gallic acid and its alkyl esters, especially propyl gallate, uric acid and its salts and alkyl esters, sorbic acid and its salts, amines (e.g., N,N-diethylhydroxylamine, aminoguanidine), sulfhydryl compounds (e.g., glutathione), dihydroxy fumaric acid and its salts, lycine pidolate, arginine pilolate, nordihydroguaiaretic acid, bioflavonoids, lysine, methionine, proline, superoxide dismutase, silymarin, tea extracts, grape skin/seed extracts, melanin, and rosemary extracts may be used. Preferred anti-oxidants/radical scavengers are selected from tocopherol sorbate and other esters of tocopherol, more preferably tocopherol sorbate. For example, the use of tocopherol sorbate in topical compositions and applicable to the present invention is described in U.S. Pat. No. 4,847,071, issued on Jul. 11, 1989 to Donald L. Bissett, Rodney D. Bush and Ranjit Chatterjee.

Of course, those skilled in the art will take care to select any additional compounds and/or quantities thereof, so as ensure that the advantageous properties of the composition according to the invention will not, substantially not, be altered by the contemplated addition.

The procedure for manufacture of the compositions according to the invention do not differ in any way form the procedures conventionally used in the cosmetics field and are entirely known to the specialist. These procedures consist in mixing the different constituents of the composition, preferably after heating, then in pouring them to produce the desired shape.

The compositions according to the invention may take the form of sticks or of flexible or poured pastes, or a viscous liquid, depending upon the desired end use of the cosmetic composition according to the present invention.

In one embodiment, the cosmetic composition of the present invention is a lip color and, if a top coat composition is provided, it may contain natural animal and vegetable fats and oils, and semi-synthetic fats and oils, examples of which include avocado oil, linseed oil, almond oil, Chinese wax, perilla oil, olive oil, cacao butter, kapok wax, kaya oil, carnauba wax, liver oil, candellila wax, beef tallow, beef foot oil, beef bone fat, hydrogenated beef tallow, apricot kernel oil, spermaceti, hydrogenated oil, wheat germ oil, sesame oil, rice germ oil, rice bran oil, sugar cane wax, sasanqua oil, safflower oil, shea butter, Chinese tung oil, cinnamon oil, jojoba wax, shellac wax, turtle oil, soybean oil, tea seed oil, tsubaki oil, evening primrose oil, corn oil, lard, rape seed oil, Japanese tung oil, rice-bran wax, germ oil, horse fat, persic oil, palm oil, palm kernel oil, castor oil, hydrogenated castor oil, caster oil fatty acid methyl ester, sunflower oil, grape seed oil, bayberry wax, jojoba oil, macadamia nut oil, bees wax, mink oil, cottonseed oil, cotton wax, Japan wax haze kernel oil, montan wax, coconut oil, hydrogenated coconut oil, tricoconut oil fatty acid glyceride, mutton-tallow, peanut oil, lanolin, liquid lanolin, reduced lanolin, lanolin alcohol, hard lanolin, lanolin acetate, lanolin fatty acid isopropyl, hexyl laurate, POE lanolin alcohol ether, POE lanolin alcohol acetate, lanolin fatty acid polyethylene glycol, POE hydrogenated lanolin alcohol ether, and egg yolk oil. Additionally, the term "POE" as used herein stands for polyoxyethylene.

Example

A long-wearing lip color is provided. It can be provided as a single step product, wherein the long-wearing color and the desired glossy finish are provided in a single application, such as in a lip stick or a liquid lip color applied with a wand or brush. Alternatively, a long-wearing lip color is a two-part system, wherein the first part applied to the lips contains the color and, once dried, a second clear part is applied over the color. While not wishing to be bound by any particular theory, it is believed that the film former in combination with the de-tackifying agent provide the longer, smoother and more comfortable wear. In so doing, the user does not experience the typical tightening of the lip tissue after application which may cause a tacky and/or flaky feel to the lip area and may exhibit a cracked appearance, as may be experience with conventional long-wearing-type lip products.

| First Color Part: | | |
|---|---|---|
| Component | Intended Purpose | Wt. % of total |
| Isodecane | Volatile/carrier | 50 |
| *Bis-PEG-1 Dimethicone-Polypropylene Glycol-26/IPDI Copolymer | Film former | 20 |
| Bentone Gel-Isododecane/disteardimonium hectorite/prop. carb. | A clay suspending agent | 10 |
| Lovely 439687 | Fragrance | 0.20 |
| Acrylate Copolymer | Matrix provided for fragrance trapping | 0.20 |
| Tetradibutyl pentaerithrityl hydroxyhydrocinnamate | Anti-oxidant | 0.05 |
| Titanium dioxide | Colorant | 4.12 |
| Iron oxide red 34-2045 | Colorant (may vary, depending upon desired shade of product) | 2.38 |
| D&C Red No. 6 Barrium Lake | Colorant (may vary, depending upon desired shade of product) | 0.90 |
| Sericite | Extender/filler/pigment jet milling processing aid | 2.55 |
| Dimethicone/vinyl dimethicone crosspolymer/silica blend | De-tackifying agent | 9.1 |
| Caprylyl glycol | Antimicrobial agent | 0.50 |

*The full chemical description of the film former is: polydimethylsiloxane-ethyleneoxyl-1 polymer and polypropyleneglycol-26 with 3 isocyanatomethyl-3,5,5-triethylcyclohexyl isocyanate.

| Second clear part: | | |
|---|---|---|
| Component | Intended Purpose | Wt. % of total |
| Polybutene | Film former | 66.84 |
| Hydrogenate polyisobutene | Emollient | 27.0 |
| Jojoba oil/gellants/BHT Hi viscosity | Moisturizer | 5.5 |
| Lovely 439687 | Fragrance | 0.20 |
| Hydroxystearic acid | Thickener | 0.26 |
| Benzoic acid | Preservative | 0.20 |

All patents and patent publications referred to herein are hereby incorporated by reference. Certain modifications and improvements will occur to those skilled in the art upon a reading of the foregoing description. It should be understood that all such modifications and improvements have been deleted herein for the sake of conciseness and readability but are properly within the scope of the following claims.

What is claimed is:

1. A cosmetic composition comprising from about 2-30% by weight of one or more coloring agents and from about 2-40% by weight of a film-forming silicone-containing polyurethane having a viscosity of about 130,000 to about 2,500,000 cps, said film-forming silicone containing polyurethane polymer is a bis-PEG-1 dimethicone-polypropylene glycol-26/isophorone diisocyante (IPDI) copolymer and being present in an effective amount to a impart long lasting transfer resistant film when applied to a surface of the human body.

* * * * *